(12) United States Patent
Domingo Coto et al.

(10) Patent No.: US 7,799,925 B2
(45) Date of Patent: Sep. 21, 2010

(54) PROCESS FOR THE PREPARATION OF THE (S)-ENANTIOMER OF OMEPRAZOLE

(75) Inventors: Antonio Domingo Coto, Barcelona (ES); Alexander Comely, Barcelona (ES); Xavier Verdaguer Espaulella, Vic (ES); Llorenç Rafecas Jané, Llorenç del Penedès (ES)

(73) Assignee: Unión Químico Farmacéutica, S.A., Barcelona (ES)

( * ) Notice: Subject to any disclaimer, the term of this patent is extended or adjusted under 35 U.S.C. 154(b) by 0 days.

(21) Appl. No.: 12/159,565

(22) PCT Filed: Dec. 18, 2006

(86) PCT No.: PCT/EP2006/069847

§ 371 (c)(1),
(2), (4) Date: Jun. 27, 2008

(87) PCT Pub. No.: WO2007/074099

PCT Pub. Date: Jul. 5, 2007

(65) Prior Publication Data

US 2008/0300411 A1 Dec. 4, 2008

(30) Foreign Application Priority Data

Dec. 28, 2005 (EP) .................................. 05113020

(51) Int. Cl.
*C07D 401/12* (2006.01)
(52) U.S. Cl. .................................. 546/273.7
(58) Field of Classification Search ............... 546/273.7
See application file for complete search history.

(56) References Cited

U.S. PATENT DOCUMENTS 5,693,818 A 12/1997 Von Unge

FOREIGN PATENT DOCUMENTS

| CN | 1223262 | 7/1999 |
| DE | 4035455.5 A1 | 5/1992 |
| EP | 0005129 A1 | 10/1979 |
| GB | 2376231 | 12/2002 |
| WO | WO 9208716 A1 | 5/1992 |
| WO | WO 9427988 A1 | 12/1994 |
| WO | WO 9602535 A1 | 2/1996 |
| WO | WO 9828294 A1 | 7/1998 |
| WO | WO 02098423 A1 | 12/2002 |
| WO | WO 2007013743 A1 | 2/2007 |

OTHER PUBLICATIONS

Vippagunta et al., "Crystalline Solid", Advanced Drug Delivery Reviews 48 (2001) 3-26.*
Guillory (in Brittain ed), "Polymorphism, etc.," NY: Marcel Dekker, Inc., 1999, 1-2, 183-226.*
Vinogradov, M.G., et al., "Efficient resolution of (±)-pantolactone by inclusion crystallization with the use of chiral 1,1,2-triphenylethane-1,2-diol", Russian Chemical Bulletin, Int.Edition, 2000, pp. 1483-1484, vol. 49, No. 8, Kluwer Academic/Plenum Publishers.
European Patent Office, International Search Report for International Application No. PCT/EP2006-069847, May 18, 2007.

* cited by examiner

*Primary Examiner*—Patricia L Morris
(74) *Attorney, Agent, or Firm*—Peter B. Scull; Kristina M. Kalan; Berenbaum Weinshienk PC

(57) ABSTRACT

A process for the preparation of (S)-omeprazole from racemic omeprazole via the formation of an inclusion complex with (S)-1,1,2-triphenyl-1,2-ethanediol. (S)-Omeprazole is recovered in a substantially optically pure form either in neutral form or as a pharmaceutically acceptable salt or as its solvates including hydrates. The (S)-omeprazole 2[(S)-1,1,2-triphenyl-1,2-ethanediol] inclusion complex is new. This resolution process proceeds with high yields and high optical purity.

18 Claims, No Drawings

PROCESS FOR THE PREPARATION OF THE (S)-ENANTIOMER OF OMEPRAZOLE

The present invention relates to a process for the preparation of the (S)-enantiomer of omeprazole and its pharmaceutically acceptable salts and solvates, including hydrates. The invention also provides a novel intermediate useful for the preparation of enantiomerically pure (S)-omeprazole.

BACKGROUND ART

The compound omeprazole of formula (I) and chemical name (5-methoxy-2-[[(4-methoxy-3,5-dimethyl-2-pyridinyl)methyl]sulfinyl]-1H-benzimidazole), and therapeutically acceptable salts thereof, is well known as an effective gastric acid secretion inhibitor and is useful as an anti-ulcer agent as was first described in EP 0005129.

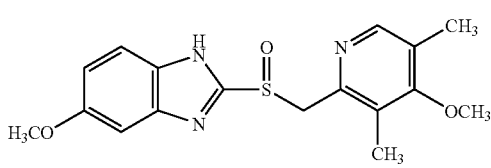
(I)

The sulphur atom of the sulfoxide group in asymmetrically substituted sulfoxides, as in omeprazole, is chiral. Therefore, omeprazole has two enantiomeric forms, the (R) and (S)-enantiomers, otherwise known as (R)-omeprazole and (S)-omeprazole, and normally exists as a racemic mixture. (S)-Omeprazole, with structural formula (II), is referred to as esomeprazole.

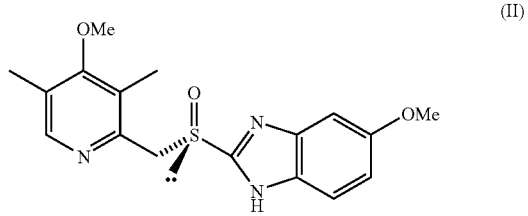
(II)

Certain methods for the preparation or separation of the enantiomers of omeprazole are known in the art. For example, DE 4035455 relates to a resolution process of omeprazole via formation of diastereomeric 1-substituted benzimidazole derivatives which are separated and thereafter hydrolysed in acidic solution. The enantiomers of omeprazole are unstable to the acidic conditions required for hydrolysis of the attached group and the acid has to be rapidly neutralised with a base to avoid excessive degradation. Moreover, the enantiomers of omeprazole are unstable to temperatures in excess of 50-60° C. The exothermicity of rapid neutralisation will lead to further degradation and is difficult to handle in large scale production.

WO 94/27988 discloses a reaction between a 6-methoxy-1-chloromethyl analogue of omeprazole and (R)-mandelic acid sodium salt in chloroform, resulting in a diastereomeric mixture which may be separated by reverse phase chromatography and subsequently hydrolysed to afford both enantiomers of omeprazole.

WO 96/02535 discloses a process for the preparation of the single enantiomers of omeprazole by asymmetric oxidation of the corresponding prochiral sulphide. The process employs an oxidizing agent and a chiral titanium complex which may include a titanium (IV) compound.

(S)-Omeprazole in a neutral, solid form (which can be in a partly or substantially crystalline state) is first described in WO 98/28294.

WO 02/098423 relates to an inclusion complex of (S)-omeprazole with cyclodextrins. The process comprises adding a cyclodextrin to an aqueous solution of a substantially pure optical isomer of a benzimidazole compound or a pharmaceutically acceptable salt thereof, and isolating the inclusion complex so formed from the solution.

CN 1223262 relates to a process for the preparation of optically pure anti-peptic ulcer benzimidazole drugs, including esomeprazole. The method makes use of bi-2-naphtol, bi-2-phenanthrol, or tartaric acid derivatives as inclusion complexation hosts for the resolution of racemic omeprazole. The method comprises dissolving racemic omeprazole and the inclusion host [preferably 2,2'-dihydroxy-1,1'-binaphthyl (BINOL)] in a benzene/hexane mixture. The enantiomeric excess (e.e.) of the inclusion complex obtained can be increased by consecutive recrystallisations. The inclusion complex is separated on a $SiO_2$ column to give (S)-omeprazole.

Despite the teaching of this prior art, there still remains a need for a new process for the preparation of substantially optically pure (S)-isomer of omeprazole and its pharmaceutically acceptable salts and solvates, including hydrates.

SUMMARY OF THE INVENTION

The present invention provides an alternative process for the preparation of substantially optically pure (S)-omeprazole and its pharmaceutically acceptable salts and solvates, including hydrates. The inventors have found that (S)-1,1,2-triphenyl-1,2-ethanediol of formula (III) is a highly effective inclusion host for the (S)-enantiomer of a racemic mixture of omeprazole, leading to (S)-omeprazole by a short and efficient process which proceeds with both high enantiomeric excess (e.e.) and yield.

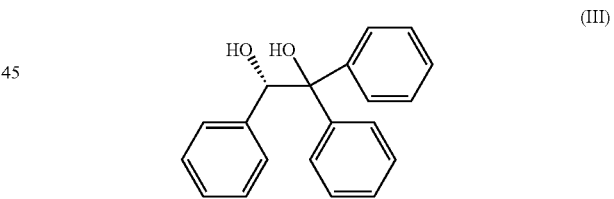
(III)

Accordingly, one aspect of the present invention is the provision of a process for the enantioselective preparation of (S)-omeprazole (II) substantially optically pure and its pharmaceutically acceptable salts and solvates including hydrates, which comprises the following steps:

a) treating racemic omeprazole of formula (I) with (S)-1,1,2-triphenyl-1,2-ethanediol of formula (III) in a suitable solvent whereby the corresponding (S)-omeprazole optical isomer forms an inclusion complex with said (S)-1,1,2-triphenyl-1,2-ethanediol which is isolated from the reaction mixture as (S)-omeprazole.2[(S)-1,1,2-triphenyl-1,2-ethanediol] of formula (IV); b) optionally, carrying out a recrystallisation or digestion of said inclusion complex; and c) separating (S)-omeprazole from (S)-1,1,2-triphenyl-1,2-ethanediol by destroying the inclusion complex of step a) or b) and recovering (S)-omeprazole in a substantially optically pure form either in neutral form or as a pharmaceutically acceptable salt; and optionally d) if a neutral form is obtained, treating with an alkaline or alkaline earth metal base in order to obtain (S)-omeprazole in a substantially optically pure form as an alkaline or alkaline earth metal salt.

A second aspect of the present invention provides a suitable intermediate used in the preparation of (S)-omeprazole that is substantially optically pure and a process for its preparation.

Accordingly, the intermediate provided by the second aspect of the invention, is the inclusion complex (S)-omeprazole.2[(S)-1,1,2-triphenyl-1,2-ethanediol] of formula (IV).

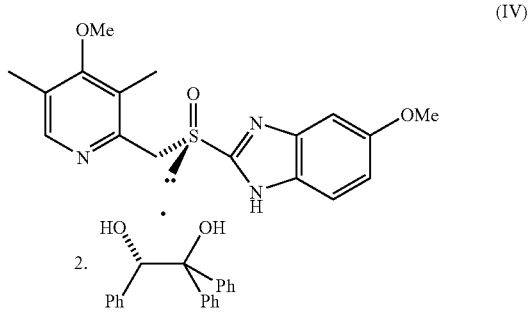

The process of the present invention offers several striking advantages: it proceeds with high yield and high enantiomeric purity; the resolution agent employed is commercially available and has a low price compared with resolution agents used previously and can be readily recovered after effecting the resolution; the process is easily industrialisable; it uses non-toxic or low-toxicity solvents; there is no need for chromatographic separations; it can be carried out under very mild conditions ensuring the integrity of (S)-omeprazole which displays a low stability to acidic conditions, high humidity, moderately elevated temperature and organic solvents. Furthermore, the inclusion complex (S)-omeprazole.2[(S)-1,1,2-triphenyl-1,2-ethanediol] of formula (IV) is very stable and is easy to handle which is advantageous in large scale production.

DETAILED DESCRIPTION OF THE INVENTION

A "substantially optically pure" isomer in the context of the present invention means an isomer with an enantiomeric excess (e.e.) suitable for a chiral compound prepared on industrial scale. Such e.e. values are readily determined by a person skilled in the art in the detection of such e.e. Usually, a process is suitable for preparation on industrial scale with an e.e. of at least 85%, preferably of at least 90% and more preferably of at least 95% e.e.

Preferably, the molar ratio is from 1 to 3 mol of (S)-1,1,2-triphenyl-1,2-ethanediol per mol of racemic omeprazole. More preferably, the ratio molar is 1.5 mol of (S)-1,1,2-triphenyl-1,2-ethanediol per mol of racemic omeprazole.

In a preferred embodiment of the first aspect of the present invention, the suitable solvent of step a) is selected from the group consisting of ($C_6$-$C_9$) aromatic hydrocarbons, ($C_5$-$C_8$) aliphatic hydrocarbons, ($C_1$-$C_5$) alcohols, ($C_3$-$C_6$) ketones, ($C_2$-$C_8$) aliphatic ethers, ($C_7$-$C_8$) aromatic ethers, acetonitrile, ($C_1$-$C_9$) halogenated aromatic or aliphatic hydrocarbons, and mixtures thereof. More preferably, said solvent is selected from the group consisting of isopropyl alcohol, methyl isobutyl ketone, toluene, ethanol, xylene, anisole, chloroform, acetonitrile, and toluene/heptane mixtures.

In a particular embodiment, the process involves heating omeprazole and (S)-1,1,2-triphenyl-1,2-ethanediol at elevated temperature in the minimum volume of the solvent or solvent mixture required to effect dissolution, and subsequent cooling. In another particular embodiment, the process involves suspending omeprazole and (S)-1,1,2-triphenyl-1,2-ethanediol in a suitable solvent at ambient temperature. Both embodiments result in the formation of a suspension of (S)-omeprazole.2[(S)-1,1,2-triphenyl-1,2-ethanediol] which is isolated by filtration. Ambient temperature resolutions may require extended reaction times to obtain high e.e. Nevertheless, on an industrial scale, it can be advantageous to use mild conditions for economic and environmental reasons and also because the degradation of the (S)-omeprazole is minimised. Accordingly, the complex formation can be carried out from ambient to reflux temperature of the solvent.

The formation of the inclusion complex can also be carried out from an aqueous solution of omeprazole sodium salt in the presence of a water-miscible solvent and (S)-1,1,2-triphenyl-1,2-ethanediol. Neutralisation with acid results in the formation of a suspension of the same inclusion complex (S)-omeprazole.2[(S)-1,1,2-triphenyl-1,2-ethanediol] which is isolated by filtration.

A preferred embodiment of the process of the present invention described herein comprises a recrystallisation or digestion of the inclusion complex (step b), thereby resulting in a considerable rise in e.e. reproducibly giving (S)-omeprazole.2[(S)-1,1,2-triphenyl-1,2-ethanediol] of >99% e.e. Recrystallisation or digestion can be effected in the same solvents as those detailed for the complex formation and can be carried out from ambient to reflux temperature of the solvent.

According to an embodiment of the present invention, the destruction step of the inclusion complex (step c) is carried out in a suitable solvent system which comprises water and which may comprise at least one water-immiscible solvent or poorly water-miscible solvent.

In a preferred embodiment, step c) comprises destroying the inclusion complex obtained with a base. Preferably, the base is selected from the group consisting of an alkaline metal hydroxide and an alkaline earth metal hydroxide. More preferably, the alkaline metal hydroxide is selected from sodium hydroxide and potassium hydroxide.

Preferably, step c) comprises treating the inclusion complex with aqueous sodium hydroxide or potassium hydroxide and a suitable solvent, preferably selected from toluene, methyl isobutyl ketone and dichloromethane. In a particularly preferred embodiment, the aqueous phase is subsequently washed with the appropriate organic solvent and is stripped to remove traces of the same.

In a preferred embodiment, following treatment with a base, the process of step c) comprises treating the resulting (S)-omeprazole salt solution with a compound selected from the group consisting of an acid, a salt thereof and mixtures thereof in order to neutralise the reaction medium to pH 7 to 9, isolating (S)-omeprazole in a substantially optically pure form, and optionally transforming the product into a pharmaceutically acceptable salt. Preferably, the acid is a carboxylic acid and the salt thereof is the ammonium salt of the acid.

According to a more preferred embodiment, following the destruction of the inclusion complex and the neutralisation treatment, neutral (S)-omeprazole precipitates and can be isolated by filtration.

In another preferred embodiment, step c) comprises seeding with (S)-omeprazole before neutralising the reaction medium.

Alternatively, the neutralisation can be carried out in the presence of a water-immiscible solvent whereby (S)-omeprazole is isolated from the organic phase by elimination of the solvent. Preferably, the water-immiscible solvent is selected from the group consisting of ($C_6$-$C_9$) aromatic hydrocarbons, ($C_5$-$C_8$) aliphatic hydrocarbons, ($C_2$-$C_8$) aliphatic ethers, ($C_7$-$C_8$) aromatic ethers, ($C_1$-$C_9$) halogenated aromatic or aliphatic hydrocarbons, and mixtures thereof. Particularly preferred are toluene, dichloromethane and tert-butyl methyl ether. When the neutralisation step is carried out in the presence of a water-immiscible solvent, further steps of washing and removal of the solvent may be required.

Alternatively, without prior neutralisation, the alkaline or alkaline earth metal salt of (S)-omeprazole can be isolated directly in a substantially optically pure form from the aqueous phase by conventional methods. The alkaline metal cation can be interconverted prior to isolation by treatment with an appropriate alkaline earth metal salt such as an alkaline earth halide such as magnesium chloride as described in WO 94/27988, for example.

Furthermore, neutral (S)-omeprazole can be subsequently converted into an (S)-omeprazole salt with an appropriate base by conventional methods, in particular into an alkaline or alkaline earth metal salt such as a sodium or magnesium salt.

The inclusion host (S)-1,1,2-triphenyl-1,2-ethanediol used in the present invention can be recovered and recycled since its optical purity remains unchanged after the resolution (step a), recrystallisation or digestion (step b), and (S)-omeprazole isolation (step c).

(R)-Omeprazole and (S)-1,1,2-triphenyl-1,2-ethanediol can be recovered from the filtrate of step a) and can subsequently be separated, recovered and recycled.

According to a preferred embodiment, (S)-1,1,2-triphenyl-1,2-ethanediol can be recovered from the filtrate separated after filtration of (S)-omeprazole.2[(S)-1,1,2-triphenyl-1,2-ethanediol] by treatment with an aqueous base, concentration of the organic phase and crystallisation.

(S)-1,1,2-Triphenyl-1,2-ethanediol can also be recovered after (S)-omeprazole isolation. Hence, the organic phase separated after basic aqueous destruction of (S)-omeprazole.2[(S)-1,1,2-triphenyl-1,2-ethanediol] is washed and concentrated to effect crystallisation of (S)-1,1,2-triphenyl-1,2-ethanediol.

The use of recovered (S)-1,1,2-triphenyl-1,2-ethanediol to carry out the resolution and recrystallisation or digestion also results in (S)-omeprazole.2[(S)-1,1,2-triphenyl-1,2-ethanediol] in excellent e.e. as is shown in the examples.

The most adequate conditions for carrying out said processes such as, for example, the concentration, temperature, solvent used, and the like can be readily determined by a person skilled in the art from routine tests and with the help of the teachings of the examples given in this description.

Throughout the description and claims the word "comprise" and variations of the word such as "comprising", are not intended to exclude other technical features, additives, components, or steps.

In order that this invention may be better understood, the following examples are set forth to illustrate various aspects of the present invention. These examples are for the purpose of illustration only and are not to be construed as limiting the scope of the invention or the scope of the claims in any manner.

EXAMPLES

Example 1

Preparation of (S)-omeprazole.2[(S)-1,1,2-triphenyl-1,2-ethanediol] in toluene/heptane A mixture of omeprazole (5 g, 14.5 mmol) and (S)-1,1,2-triphenyl-1,2-ethanediol (6.30 g, 21.7 mmol) was dissolved in a minimum of a toluene/heptane mixture (0.84:0.16, 190 ml) at 100° C. On dissolution, the solution was cooled to ambient temperature slowly with vigorous stirring, and on reaching this temperature was stirred for a further 1 h. The precipitate was filtered, was washed with a toluene/heptane mixture (3:1, 2×50 ml) and was dried in vacuo to afford (S)-omeprazole.2[(S)-1,1,2-triphenyl-1,2-ethanediol] inclusion complex (6.108 g, 91%, 96.3% e.e.) as an off-white powder.

Example 2

Preparation of (S)-omeprazole.2[(S)-1,1,2-triphenyl-1,2-ethanediol] in toluene

A mixture of omeprazole (250 mg, 0.72 mmol) and (S)-1,1,2-triphenyl-1,2-ethanediol (315 mg, 1.08 mmol) was dissolved in a minimum volume of toluene (11 ml) at 90° C. On dissolution, the solution was cooled to ambient temperature slowly with vigorous stirring, and on reaching this temperature was stirred for a further 1 h. The precipitate was filtered, was washed with toluene (2×3 ml) and was dried in vacuo to afford (S)-omeprazole.2[(S)-1,1,2-triphenyl-1,2-ethanediol] inclusion complex (291 mg, 87%, 95% e.e.) as an off-white powder.

Example 3

Preparation of (S)-omeprazole.2[(S)-1,1,2-triphenyl-1,2-ethanediol] in isopropyl alcohol A mixture of omeprazole (250 mg, 0.72 mmol) and (S)-1,1,2-triphenyl-1,2-ethanediol (315 mg, 1.08 mmol) was dissolved in a minimum volume of isopropyl alcohol (10 ml) at reflux temperature. On dissolution, the solution was cooled to ambient temperature slowly with vigorous stirring, and on reaching this temperature was stirred for a further 1 h. The precipitate was filtered, was washed with isopropyl alcohol (2×2 ml) and was dried in vacuo to afford (S)-omeprazole.2 [(S)-1,1,2-triphenyl-1,2-ethanediol] inclusion complex (240 mg, 72%, 97% e.e.) as an off-white powder.

Example 4

Preparation of (S)-omeprazole.2[(S)-1,1,2-triphenyl-1,2-ethanediol] in methyl isobutyl ketone A mixture of omeprazole (250 mg, 0.72 mmol) and (S)-1,1,2-triphenyl-1,2-ethanediol (315 mg, 1.08 mmol) was dissolved in a minimum volume of methyl isobutyl ketone (8 ml) at 90° C. On dissolution, the solution was cooled to ambient temperature slowly with vigorous stirring, and on reaching this temperature was stirred for a further 1 h. The precipitate was filtered, was washed with methyl isobutyl ketone (2×2 ml) and was dried in vacuo to afford (S)-omeprazole.2[(S)-1,1,2-triphenyl-1,2-ethanediol] inclusion complex (253 mg, 76%, 94% e.e.) as an off-white powder.

Example 5

Preparation of (S)-omeprazole.2[(S)-1,1,2-triphenyl-1,2-ethanediol] in anisole

A mixture of omeprazole (250 mg, 0.72 mmol) and (S)-1,1,2-triphenyl-1,2-ethanediol (315 mg, 1.08 mmol) was dissolved in a minimum volume of anisole (4 ml) at 90° C. On dissolution, the solution was cooled to ambient temperature slowly with vigorous stirring, and on reaching this temperature was stirred for a further 1 h. The precipitate was filtered, was washed with anisole (2×2 ml) and was dried in vacuo to afford (S)-omeprazole.2[(S)-1,1,2-triphenyl-1,2-ethanediol] inclusion complex (215 mg, 64%, 96% e.e.) as an off-white powder.

Example 6

Preparation of (S)-omeprazole.2[(S)-1,1,2-triphenyl-1,2-ethanediol] in acetonitrile A mixture of omeprazole (250 mg, 0.72 mmol) and (S)-1,1,2-triphenyl-1,2-ethanediol (315 mg, 1.08 mmol) was dissolved in a minimum volume of acetonitrile (4 ml) at reflux temperature. On dissolution, the solution was cooled to ambient temperature slowly with vigorous stirring, and on reaching this temperature was stirred for a further 1 h. The precipitate was filtered, was washed with acetonitrile (2×2 ml) and was dried in vacuo to afford (S)-omeprazole.2[(S)-1,1,2-triphenyl-1,2-ethanediol] inclusion complex (239 mg, 71%, 95% e.e.) as an off-white powder.

Example 7

Preparation of (S)-omeprazole.2[(S)-1,1,2-triphenyl-1,2-ethanediol] in chloroform A mixture of omeprazole (250 mg, 0.72 mmol) and (S)-1,1,2-triphenyl-1,2-ethanediol (315 mg, 1.08 mmol) was dissolved in a minimum volume of chloroform (4 ml) at reflux temperature. On dissolution, the solution was cooled to ambient temperature slowly with vigorous stirring, and on reaching this temperature was stirred for a further 1 h. The precipitate was filtered, was washed with chloroform (2×2 ml) and was dried in vacuo to afford (S)-omeprazole.2[(S)-1,1,2-triphenyl-1,2-ethanediol] inclusion complex (141 mg, 42%, 94% e.e.) as an off-white powder.

Example 8

Preparation of (S)-omeprazole.2[(S)-1,1,2-triphenyl-1,2-ethanediol]: recycling of (S)-1,1,2-triphenyl-1,2-ethanediol A mixture of omeprazole (500 mg, 1.45 mmol) and (S)-1,1,2-triphenyl-1,2-ethanediol (630 mg, 2.17 mmol, 99.3% e.e. recovered according to Example 24) was dissolved in a minimum volume of toluene (18 ml) at 90° C. On dissolution, the solution was cooled to ambient temperature slowly with vigorous stirring, and on reaching this temperature was stirred for a further 1 h. The precipitate was filtered, was washed with toluene (2×5 ml) and was dried in vacuo to afford (S)-omeprazole.2[(S)-1,1,2-triphenyl-1,2-ethanediol] inclusion complex (627 mg, 94%, 93.7% e.e.) as an off-white powder.

Example 9

Preparation of (S)-omeprazole.2[(S)-1,1,2-triphenyl-1,2-ethanediol] in ethanol

A suspension of omeprazole (20 g, 57.9 mmol) and (S)-1,1,2-triphenyl-1,2-ethanediol (25.2 g, 86.9 mmol) in ethanol (700 ml) at ambient temperature was stirred for 30 h. The solid was filtered, was washed with ethanol (2×150 ml) and was dried in vacuo to afford (S)-omeprazole.2[(S)-1,1,2-triphenyl-1,2-ethanediol] (24.1 g, 90%, 95.5% e.e.) as a white powder.

Example 10

Preparation of (S)-omeprazole.2[(S)-1,1,2-triphenyl-1,2-ethanediol] in anisole

A suspension of omeprazole (250 mg, 0.72 mmol) and (S)-1,1,2-triphenyl-1,2-ethanediol (315 mg, 1.09 mmol) in anisole (8.8 ml) at ambient temperature was stirred for 72 h. The solid was filtered, was washed with anisole (2×2 ml) and was dried in vacuo to afford (S)-omeprazole.2[(S)-1,1,2-triphenyl-1,2-ethanediol] (265 mg, 79%, 96.6% e.e.) as a white powder.

Example 11

Preparation of (S)-omeprazole.2[(S)-1,1,2-triphenyl-1,2-ethanediol] in methyl isobutyl ketone A suspension of omeprazole (250 mg, 0.72 mmol) and (S)-1,1,2-triphenyl-1,2-ethanediol (315 mg, 1.09 mmol) in methyl isobutyl ketone (8.8 ml) at ambient temperature was stirred for 72 h. The solid was filtered, was washed with methyl isobutyl ketone (2×2 ml) and was dried in vacuo to afford (S)-omeprazole.2[(S)-1,1,2-triphenyl-1,2-ethanediol] (286 mg, 69.1% e.e.) as a white powder.

Example 12

Preparation of (S)-omeprazole.2[(S)-1,1,2-triphenyl-1,2-ethanediol] in toluene

A suspension of omeprazole (250 mg, 0.72 mmol) and (S)-1,1,2-triphenyl-1,2-ethanediol (315 mg, 1.09 mmol) in toluene (8.8 ml) at ambient temperature was stirred for 18 h. The solid was filtered, was washed with toluene (2×2 ml) and was dried in vacuo to afford (S)-omeprazole.2[(S)-1,1,2-triphenyl-1,2-ethanediol] (320 mg, 96%, 94.6% e.e.) as a white powder.

Example 13

Preparation of (S)-omeprazole.2[(S)-1,1,2-triphenyl-1,2-ethanediol] from omeprazole sodium To aqueous sodium hydroxide (2.03 ml, 1.5 M, 3.04 mmol) at ambient temperature was added omeprazole (1 g, 2.90 mmol) in 5 portions over 10 min. On complete dissolution, ethanol (35 ml) and (S)-1,1,2-triphenyl-1,2-ethanediol (1.26 g, 4.34 mmol) were added. To the resulting colourless solution at ambient temperature was added a solution of aqueous acetic acid (3.04 ml, 1 M, 3.04 mmol) dropwise over 1 h and, on complete addition, stirring was continued for 4 h. The solid was filtered, was washed with ethanol (3×15 ml) and was dried in vacuo to afford (S)-omeprazole.2[(S)-1,1,2-triphenyl-1,2-ethanediol] (925 mg, 69%, 96.4% ee) as a white powder.

Example 14

Recrystallisation of (S)-omeprazole.2[(S)-1,1,2-triphenyl-1,2-ethanediol] in isopropyl alcohol (S)-omeprazole.2[(S)-1,1,2-triphenyl-1,2-ethanediol] (250 mg, 0.27 mmol, 96.3% e.e.) was dissolved in isopropyl alcohol (5.8 ml) at reflux temperature and the solution was allowed to cool to ambient temperature over 30 min. After stirring at 0° C. for a further 30 min, the mixture was filtered and the collected solid was washed with isopropyl alcohol (2×2 ml at 0° C.) and dried in vacuo to afford (S)-omeprazole.2[(S)-1,1,2-triphenyl-1,2-ethanediol] (167 mg, 67%, 99.9% e.e.).

Rf (SiO$_2$, CH$_2$Cl$_2$/MeOH 9:1) 0.78 (1,1,2-triphenyl-1,2-ethanediol) and 0.50 (omeprazole).

IR (KBr: w weak, m medium, s strong) 3533w, 3394m, 3056w, 1624w, 1572w, 1493m, 1448s, 1309w, 1269m, 1232m, 1197m, 1153m, 1116m, 1075s, 1043s, 974m, 929w, 896w, 828m, 762m, 736s, 698s and 614m $^1$H NMR (400 MHz, DMSO-D$_6$, (S)-omeprazole E, 1,1,2-triphenyl-1,2-ethanediol T) 13.4 (brs, 1H, E), 8.19 (s, 1H), 7.58 (d, J=7.2 Hz, 4H, T), 7.55 (d, J=7 Hz, 1H, E), 7.29-7.02 (m, 26H, T), 6.93 (dd, J=2.4 and 9.2 Hz, E), 5.56 (brs, 4H, T OH and PhCH), 5.48 (s, 2H, T OH), 4.77 (d, J=13.6 Hz, E), 4.68 (d, J=13.6 Hz, E), 3.81 (s, 3H, E), 3.68 (s, 3H, E), 2.20 (s, 3H, E) and 2.17 (s, 3H, E).

$^{13}$C NMR (101 MHz, DMSO-D$_6$, (S)-omeprazole E, 1,1,2-triphenyl-1,2-ethanediol T) 163.5, 149.6, 149.1, 146.6, 146.0, 142.0, 128.7, 127.4, 127.1, 126.5, 126.34, 126.30, 126.0, 125.8, 125.5, 79.7, 76.6, 60.1, 59.7, 55.5, 12.9 and 11.1.

Example 15

Recrystallisation of (S)-omeprazole.2[(S)-1,1,2-triphenyl-1,2-ethanediol] in methyl isobutyl ketone (S)-omeprazole.2[(S)-1,1,2-triphenyl-1,2-ethanediol] (250 mg, 0.27 mmol, 96.3% e.e.) was dissolved in methyl isobutyl ketone (4.5 ml) at reflux temperature and the solution was allowed to cool to ambient temperature over 30 min. After stirring at 0° C. for a further 30 min, the mixture was filtered and the collected solid was washed with methyl isobutyl ketone (2×2 ml at 0° C.) and dried in vacuo to afford (S)-omeprazole.2[(S)-1,1,2-triphenyl-1,2-ethanediol] (197 mg, 79%, 99.8% e.e.).

Example 16

Recrystallisation of (S)-omeprazole.2[(S)-1,1,2-triphenyl-1,2-ethanediol] in toluene/heptane (S)-omeprazole.2[(S)-1,1,2-triphenyl-1,2-ethanediol] (150 mg, 0.16 mmol, 96.4% e.e.) was dissolved in toluene/heptane (3:2, 2.4 ml) at reflux temperature and the solution was allowed to cool to ambient temperature over 30 min. The mixture was filtered and the collected solid was washed with isopropyl alcohol (2×2 ml at 0° C.) and dried in vacuo to afford (S)-omeprazole.2[(S)-1,1,2-triphenyl-1,2-ethanediol] (98 mg, 65%, 99% e.e.).

Example 17

Recrystallisation of (S)-omeprazole.2[(S)-1,1,2-triphenyl-1,2-ethanediol] in toluene (S)-omeprazole.2[(S)-1,1,2-triphenyl-1,2-ethanediol] (250 mg, 0.27 mmol, 96.3% e.e.) was dissolved in toluene (7.5 ml) at 90° C. and the solution was allowed to cool to ambient temperature over 30 min. After stirring at 0° C. for a further 30 min, the mixture was filtered and the collected solid was washed with toluene (2×2 ml at 0° C.) and dried in vacuo to afford (S)-omeprazole.2[(S)-1,1,2-triphenyl-1,2-ethanediol] (208 mg, 83%, 99.8% e.e.).

Example 18

Digestion of (S)-omeprazole.2[(S)-1,1,2-triphenyl-1,2-ethanediol] in ethanol (S)-omeprazole.2[(S)-1,1,2-triphenyl-1,2-ethanediol] (23.5 g, 25.4 mmol, 95.5% e.e.) was suspended in ethanol (600 ml) at ambient temperature and was stirred for 24 h. The mixture was filtered and the collected solid was washed with ethanol (2×100 ml) and dried in vacuo to afford (S)-omeprazole.2[(S)-1,1,2-triphenyl-1,2-ethanediol] (19.1 g, 81%, 99.5% e.e.) as a white solid.

Example 19

Digestion of (S)-omeprazole.2[(S)-1,1,2-triphenyl-1,2-ethanediol] in anisole (S)-Omeprazole.2[(S)-1,1,2-triphenyl-1,2-ethanediol] (200 mg, 0.215 mmol, 96.6% e.e.) was suspended in anisole (5 ml) at ambient temperature and was stirred for 22 h. The mixture was filtered and the collected solid was washed with anisole (2×2 ml) and dried in vacuo to afford (S)-omeprazole.2[(S)-1,1,2-triphenyl-1,2-ethanediol] (145 mg, 73%, 99.4% e.e.) as a white solid.

Example 20

Isolation of (S)-omeprazole

To a suspension of (S)-omeprazole.2[(S)-1,1,2-triphenyl-1,2-ethanediol] (2.5 g, 2.7 mmol, 99.3% e.e.) in toluene (23 ml) was added aqueous sodium hydroxide (1.5 M, 1.9 ml, 2.83 mmol) and the mixture was heated at 80° C. to effect complete dissolution. The biphasic mixture was cooled to approximately 70° C. and the aqueous phase was decanted. The organic phase was extracted with water (2×4 ml) at approximately 70° C. and the combined aqueous phases were washed with toluene (2×6 ml) at ambient temperature and stripped on a rotary evaporator (40° C., 10 min). After cooling to 0° C. and seeding with (S)-omeprazole (100 mg), a solution of glacial acetic acid (163 μl, 2.83 mmol) in water (3 ml) was added dropwise over 1 h with vigorous stirring. Stirring was continued for a further 1 h at 0° C. and the mixture was filtered. The collected solid was washed with water (2×5 ml) and dried in vacuo at ambient temperature to afford (S)-omeprazole (867 mg, 98%, 99.7% e.e.) as a white solid.

Rf (SiO$_2$, CH$_2$Cl$_2$/MeOH 9:1) 0.50.

IR (KBr: w weak, m medium, s strong) 3059w, 3005w, 2904w, 2802w, 1627s, 1587m, 1567m, 1511m, 1472m, 1408s, 1311m, 1271w, 1204ss, 1186m, 1158m, 1112w, 1077m, 1016s, 966m, 885w, 822m, 810m and 430m.

¹H NMR (400 MHz, CDCl₃) 8.22 (s, 1 H), 7.53 (broad s, 1 H), 7.03 (broad s, 1 H), 6.96 (dd, J=2.4 and 8.8 Hz, 1 H), 4.79 (d, J=13.6 Hz, 1 H), 4.69 (d, J=13.6 Hz, 1 H), 3.85 (s, 3 H), 3.70 (s, 3 H), 2.24 (s, 3 H) and 2.22 (s, 3 H).

Example 21

Isolation of (S)-omeprazole

To a suspension of (S)-omeprazole.2[(S)-1,1,2-triphenyl-1,2-ethanediol] (2.5 g, 2.7 mmol, 99.3% e.e.) in toluene (23 ml) was added aqueous potassium hydroxide (1.5 M, 2.24 ml, 2.83 mmol) and the mixture was heated at 80° C. to effect complete dissolution. The biphasic mixture was cooled to approximately 70° C. and the aqueous phase was decanted. The organic phase was extracted with water (2×4 ml) at approximately 70° C. and the combined aqueous phases were washed with toluene (2×6 ml) at ambient temperature and stripped on a rotary evaporator (40° C., 10 min). After cooling to 0° C. and seeding with (S)-omeprazole (100 mg), a solution of glacial acetic acid (163 µl, 2.83 mmol) in water (3 ml) was added dropwise over 1 h with vigorous stirring. Stirring was continued for a further 1 h at 0° C. and the mixture was filtered. The collected solid was washed with water (2×5 ml) and dried in vacuo at ambient temperature to afford (S)-omeprazole (885 mg, 95%, 99.8% e.e.) as a white solid.

Example 22

Isolation of (S)-omeprazole

To a suspension of (S)-omeprazole.2[(S)-1,1,2-triphenyl-1,2-ethanediol] (2.2 g, 2.4 mmol, 99.3% e.e.) in dichloromethane (13 ml) was added aqueous sodium hydroxide (1.5 M, 1.6 ml, 2.5 mmol) and the mixture was heated to reflux temperature to effect complete dissolution. The aqueous phase was decanted and the organic phase was extracted with water (2×4 ml) at approximately 40° C. and the combined aqueous phases were washed with dichloromethane (2×5 ml) at ambient temperature. Dichloromethane (8.2 ml) was replaced and, to the biphasic mixture at 0° C., a solution of glacial acetic acid (144 µl, 2.50 mmol) in water (3 ml) was added dropwise over 1 h with vigorous stirring. The organic phase was decanted, was washed with water (2×5 ml) and was concentrated in vacuo to afford (S)-omeprazole (687 mg, 84%, 99.8% e.e.) as a white solid foam.

Example 23

Isolation of (S)-omeprazole

To a suspension of (S)-omeprazol 2 [(S)-1,1,2-triphenyl-1,2-ethanediol] (2.2 g, 2.4 mmol, 99.3% e.e.) in dichloromethane (13 ml) was added aqueous sodium hydroxide (1.5 M, 1.64 ml, 2.5 mmol) and the mixture was heated to reflux temperature to effect complete dissolution. The aqueous phase was decanted and the organic phase was extracted with water (2×4 ml) at approximately 40° C. and the combined aqueous phases were washed with dichloromethane (2×5 mL) at ambient temperature and stripped on a rotary evaporator (40° C., 10 min). After cooling to 0° C. and seeding with (S)-omeprazol (100 mg), a solution of ammonium acetate (0.2 g, 2.6 mmol) in water (3 ml) was added dropwise over 1 h with vigorous stirring. Stirring was continued for a further 1 h at 0° C. and the mixture was filtered. The collected solid was washed with water (2×5 mL) and dried in vacuo at ambient temperature to afford (S)-omeprazol (788 mg, 96%, 99.8% e.e.) as a white solid.

Example 24

Recovery of (S)-1,1,2-triphenyl-1,2-ethanediol

The organic phase decanted after separation of aqueous (ω-omeprazole sodium salt (2.7 mmol) was washed with aqueous sodium hydroxide (1 M, 5.4 ml, 5.4 mmol) and with water (2×5 ml) at approximately 70° C. The solution was concentrated to a volume of 4.5 ml and, after heating to redissolve the resulting suspension, was stirred at ambient temperature for 1 h. After further cooling to 0° C. for 30 min, the mixture was filtered and the solid collected was washed with toluene (3×1 ml at 0° C.) and dried in vacuo to give (S)-1,1,2-triphenyl-1,2-ethanediol (1.25 g, 80%, 99.9% e.e.) as a white crystalline solid.

Example 25

Recovery of (S)-1,1,2-triphenyl-1,2-ethanediol

The organic phase separated after filtration of (S)-omeprazole.2[(S)-1,1,2-triphenyl-1,2-ethanediol] (29 mmol) was concentrated to a volume of 60 ml. After treatment with aqueous sodium hydroxide (1.5 M, 16 ml, 24 mmol) at 80° C. for 10 min, the aqueous phase was decanted and the organic phase was washed with water (2×10 ml) at approximately 70° C. The solution was further concentrated to a volume of 14 ml and, after heating to redissolve the resulting suspension, was stirred at ambient temperature for 1 h. After further cooling to 0° C. for 1 h, the mixture was filtered and the solid collected was washed with toluene (2×4 ml at 0° C.) and dried in vacuo to give (S)-1,1,2-triphenyl-1,2-ethanediol (3.46 g, 82%, 99.3% e.e.) as a white crystalline solid.

The invention claimed is:

1. A process for the preparation of substantially optically pure (S)-omeprazole of formula (II), or its pharmaceutically acceptable salts;

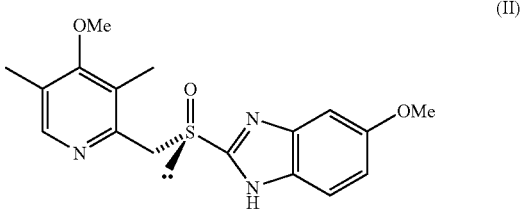

comprising the steps of:
a) treating a racemic mixture of omeprazole of formula (I) with (S)-1,1,2-triphenyl-1,2-ethanediol of formula (III) in a solvent, whereby the corresponding (S)-omeprazole optical isomer forms an inclusion complex with said (S)-1,1,2-triphenyl-1,2-ethanediol, and isolating from the reaction medium the (S)-omeprazole.2[(S)-1,1,2-triphenyl-1,2-ethanediol] inclusion complex of formula (IV) thus obtained;

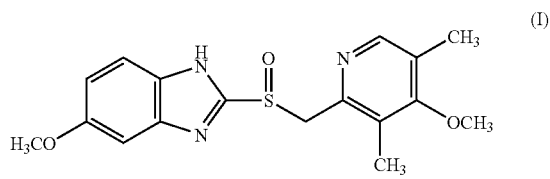

-continued

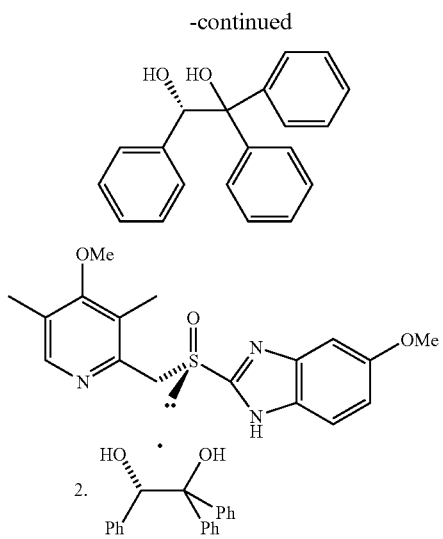

b) separating (S)-omeprazole from (S)-1,1,2-triphenyl-1,2-ethanediol by destroying the inclusion complex of step a) and recovering (S)-omeprazole in a substantially optically pure form either in neutral form or as a pharmaceutically acceptable salt.

2. The process according to claim 1 wherein the solvent used in step a) is selected from the group consisting of ($C_6$-$C_9$) aromatic hydrocarbons, ($C_5$-$C_8$) aliphatic hydrocarbons, ($C_1$-$C_5$) alcohols, ($C_3$-$C_6$) ketones, ($C_2$-$C_8$) aliphatic ethers, ($C_7$-$C_8$) aromatic ethers, acetonitrile, ($C_1$-$C_9$) halogenated aromatic or aliphatic hydrocarbons, and mixtures thereof.

3. The process according to claim 2 wherein the solvent is selected from the group consisting of isopropyl alcohol, methyl isobutyl ketone, toluene, ethanol, xylene, anisole, chloroform, acetonitrile, and toluene/heptane mixtures.

4. The process according to claims 1 wherein the destruction of the inclusion complex is carried out in a suitable solvent system which comprises water and at least one water-immiscible solvent.

5. The process according to claim 4, wherein the destruction of the inclusion complex is carried out with a base.

6. The process according to claim 5 wherein the base is selected from the group consisting of an alkaline metal hydroxide and an alkaline earth metal hydroxide.

7. The process according to claim 6 wherein the alkaline metal hydroxide is selected from sodium hydroxide and potassium hydroxide.

8. The process according to claim 4 wherein an (S)-omeprazole salt is recovered directly in a substantially optically pure form from the aqueous phase.

9. The process according to claim 4 wherein neutral (S)-omeprazole is recovered in a substantially optically pure form from the aqueous phase by adding to the reaction medium a compound selected from the group consisting of an acid, a salt thereof and mixtures thereof, followed by isolation of the product.

10. The process according to claim 9, wherein neutral (S)-omeprazole is recovered in a substantially optically pure form from the aqueous phase by adding to the reaction medium an acid followed by isolation of the product.

11. The process according to claims 9, wherein the (S)-omeprazole isolation is carried out by filtration.

12. The process according to claims 9, wherein the (S)-omeprazole recovery is carried out in the presence of a water-immiscible solvent and the (S)-omeprazole is isolated from the organic phase by elimination of the solvent.

13. The process according to claim 12 wherein the water-immiscible solvent is selected from the group consisting of ($C_6$-$C_9$) aromatic hydrocarbons, ($C_5$-$C_8$) aliphatic hydrocarbons, ($C_2$-$C_8$) aliphatic ethers, ($C_7$-$C_8$) aromatic ethers, ($C_1$-$C_9$) halogenated aromatic or aliphatic hydrocarbons, and mixtures thereof 14. The process according to claim 13, wherein the water-immiscible organic solvent is selected from the group consisting of toluene, dichloromethane and tert-butyl methyl ether.

15. The process according to claim 1, further comprising the step of carrying out a recrystallisation or digestion of the inclusion complex between steps (a) and (b).

16. The process according to claim 15 wherein a solvent is used and the solvent used is selected from the group consisting of ($C_6$-$C_9$) aromatic hydrocarbons, ($C_5$-$C_8$) aliphatic hydrocarbons, ($C_1$-$C_5$) alcohols, ($C_3$-$C_6$) ketones, ($C_2$-$C_8$) aliphatic ethers, ($C_7$-$C_8$) aromatic ethers, acetonitrile, ($C_1$-$C_9$) halogenated aromatic or aliphatic hydrocarbons, and mixtures thereof.

17. The process according to claim 9, further comprising the step of transforming the product into a pharmaceutically acceptable salt of the product.

18. The process according to claim 10, further comprising the step of transforming the product into a pharmaceutically acceptable salt of the product.

* * * * *